US006344205B1

United States Patent
Grimm et al.

(10) Patent No.: US 6,344,205 B1
(45) Date of Patent: Feb. 5, 2002

(54) ANHYDROUS COMPOSITION, COSMETIC, PHARMACEUTICAL OR HYGIENE USE

(75) Inventors: Sabine Grimm, Châtenay Malabry; Euriel Clavel, Paris, both of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/490,683

(22) Filed: Jan. 24, 2000

(51) Int. Cl.$^7$ ............... A61K 6/00; A61K 7/00; A61K 7/04; A61K 7/02; A61K 7/025
(52) U.S. Cl. ............... 424/401; 61/63; 61/64; 61/489
(58) Field of Search ............... 424/400, 401, 424/64, 69, 70.7, 61, 78.03, 489, 63

(56) References Cited

U.S. PATENT DOCUMENTS 5,679,361 A * 10/1997 Pradier et al. ............... 424/401
6,143,283 A * 11/2000 Calello et al. ............... 424/64

FOREIGN PATENT DOCUMENTS

| FR | 2 486 800 | 1/1982 |
| FR | 2 759 902 | 8/1998 |
| WO | WO 96/21422 | 7/1996 |

OTHER PUBLICATIONS

Database Chemical Abstracts, XP002118915 (JP 05 170620), Jul. 9, 1993.
Database Chemical Abstrcts, XP002118916 (JP 07 017831), Jan. 20, 1995.
English language Derwent Abstract of FR 2 486 800.
English language Derwent Abstract of FR 2 759 902.
English language translation of FR 2 759 902.

* cited by examiner

*Primary Examiner*—Thurman K. Page
*Assistant Examiner*—S. Howard
(74) *Attorney, Agent, or Firm*—Finnegan, Henderson, Farabow, Garrett & Dunner, L.L.P.

(57) ABSTRACT

The present invention is directed to a anhydrous composition, in particular a cosmetic, dermatological, hygiene or pharmaceutical composition, comprising i) an oily phase comprising isononyl isononanoate and at least one silicone oil, and ii) a particulate phase comprising at least one pulverulent compound, characterized in that the isononyl isononanoate is present in a content of at least 10% by weight, relative to the total weight of the composition, the silicone oil is present in a content of at least 5% by weight and the pulverulent compounds are present in a content of at least 10% by weight. The invention is also directed to the cosmetic applications of such a composition.

51 Claims, No Drawings

ANHYDROUS COMPOSITION, COSMETIC, PHARMACEUTICAL OR HYGIENE USE

This application claims foreign priority benefit of French Application No. 99/00829, filed Jan. 26, 1999.

The present invention relates to anhydrous cosmetic compositions, in particular cosmetic, dermatological, hygiene or pharmaceutical compositions. These compositions can constitute care products for the skin, including the scalp, and/or make-up products for the skin, mucous membranes (lips or the inside of the eyelids), semi-mucous membranes (lips), keratin fibres (hair, eyelashes, nails) or make-up products for the body.

Make-up compositions containing a fatty phase are commonly used in cosmetics on account of their good adhesion to the epidermis, their comfortable feel, their protective capacity and their capacity to form a water-impermeable film. Anhydrous make-up products are generally in the form of a compact solid or in the form of a cream. Compositions with a creamy consistency may be sought since they can be applied in a satisfactory manner using the fingers, from packaging in the form of a jar or tube. They generally contain oils and waxes in order to obtain a consistency which is stable over time.

However, one of the drawbacks of this type of product is that, due to the fact that they comprise a large amount of fatty substances, they leave the skin feeling greasy and sticky and they are difficult to spread.

The aim of the present invention is to provide an anhydrous composition, in particular in the form of a cast product, which has improved cosmetic properties and good stability. In particular, what is sought is a composition which does not give a greasy or sticky feel when applied, but which nevertheless feels soft and comfortable on the skin.

It has now been discovered, surprisingly and unexpectedly, that by using a specific fatty ester combined with pulverulent compounds in specific proportions, it is possible to obtain anhydrous compositions which spread easily on the skin, which do not feel greasy or sticky, and which have excellent cosmetic properties, in particular very great softness and good stability.

One subject of the present invention is thus an anhydrous composition, in particular a cosmetic, dermatological, hygiene or pharmaceutical composition, comprising i) at least one oily phase comprising isononyl isononanoate, and ii) at least one particulate phase comprising pulverulent compounds, characterized in that the isononyl isononanoate is present in a content of at least 10% by weight, relative to the total weight of the composition, the pulverulent compounds are present in a content of at least 10% by weight, relative to the total weight of the composition, and the oily phase also comprises a silicone oil, the said silicone oil being present in a content of greater than or equal to 5% by weight, relative to the total weight of the composition.

The invention also relates to a non-therapeutic treatment process for the skin and/or the scalp, in particular a make-up process, which consists in applying a composition as defined above to the skin or mucous membranes and/or to the scalp.

It has been found that the composition used according to the invention is particularly soft: it can be applied and spread easily and homogeneously, without leaving a greasy or sticky feel. It also has a light texture and remains comfortable to wear throughout the day.

The composition according to the invention moreover has good sensory and cosmetic qualities, in particular a good matt effect and good covering power, uniformity and staying power.

The anhydrous composition according to the invention gives a uniform, homogeneous make-up result.

Furthermore, when applied to the skin, it has the advantage of not migrating in the folds of the skin and/or in the wrinkles of the face.

The compositions of the invention are anhydrous compositions. In general, an anhydrous composition is a composition comprising less than 3% by weight of water, relative to the total weight of the composition, preferably less than 1% of water. Even more preferably, the composition comprises no water at all.

The compositions according to the invention comprise an oily phase which comprises at least 10% by weight, relative to the total weight of the composition, of a liquid fatty ester which is isononyl isononanoate. In one embodiment of the present invention, the oily phase comprises greater than 10% by weight of a liquid fatty ester which is isononyl isononanoate, relative to the total weight of the composition. An oily phase generally refers to a phase comprising fatty substances which are liquid at room temperature.

In one embodiment of the present invention, the isononyl isononanoate is present in the compositions according to the invention in a content which can range from 10 to 40% by weight, relative to the total weight of the composition. More preferably, this content ranges from 15 to 35% by weight relative to the total weight of the composition.

As commercial products corresponding to isononyl isononanoate, mention may be made of Wickenol 151 sold by the company Caschem, "Dermol 99" sold by the company Alzo or "Lanol 99" sold by the company SEPPIC.

The composition according to the invention also comprises at least one silicone oil present in a content of greater than or equal to 5% by weight relative to the total weight of the composition. In one embodiment of the present invention, the content of silicone oil ranges from 5 to 55%, more preferably from 5 to 25%, by weight and even more preferably from 10 to 25% by weight, relative to the total weight of the composition.

The silicone oil which can be used according to the invention can be chosen from:

cyclic volatile silicones containing from 3 to 8 silicon atoms, preferably 4 to 6 atom, such as, for example, cyclotetradimethylsiloxane, cyclopentadimethylsiloxane or cyclohexadimethylsiloxane; in particular the products sold under the names "DC Fluid 244", "DC Fluid 245", "DC Fluid 344" and "DC Fluid 345" by the company Dow Corning, linear volatile silicones containing from 2 to 9 silicon atoms, for example hexamethyldisiloxane, hexylheptamethyltrisiloxane and octylheptamethyltrisiloxane;

the polydimethylsiloxanes of the general formula below:

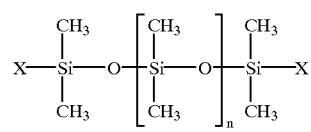

in which:

X is -CH$_3$ or OH, and n is an integer ranging from 0 to 2000, and preferably those in which the viscosity at 25° C. is less than or equal to 0.06 m$^2$/s, among which mention may be made of those sold under the name "Dow Corning Fluid 200" by the company Dow Corning; mention may also be made in particular of the products sold under the name "AK" by the company Wacker, "SF" by the company General Electric and "Abil" by the company Goldschmidt, such as the product "Abil 10", alkylmethylpolysiloxanes and in particular poly($C_1$–$C_{20}$)alkylsiloxanes such as phenylsilicone oils or cetyldimethicone (CTFA name);

cyclocopolymers of the dimethylsiloxane/ methylalkylsiloxane type, such as "silicone FZ 3109", sold by the company Union Carbide, which is a dimethylsiloxane/methyloctylsiloxane cyclocopolymer;

silicone gums which are optionally phenylated or hydroxylated polysiloxanes, with a high molecular mass of about 200,000 to 1,000,000 and with a viscosity of greater than 500,000 mPa.s, when they are dissolved in a solvent such as a polydimethylsiloxane or polyphenylsiloxane oil, or a cyclomethicone, silicone resins comprising a combination of units $R_3SiO_{1/2}$, $R_2SiO_{2/2}$, $RSiO_{3/2}$ and $SiO_{4/2}$, in which R is hydrogen, a $C_1$–$C_6$ alkyl radical or a phenyl radical, when they are dissolved in a solvent such as a polydimethylsiloxane or polyphenylsiloxane oil, or a cyclomethicone, and/or mixtures thereof.

In one embodiment, the composition according to the invention is free of phenyltrimethicone.

The oily phase can also comprise oils other than isononyl isononanoate and silicone oils. Among the other oils which can be used according to the present invention, mention may be made of:

fatty esters other than isononyl isononanoate, such as:
branched $C_8$–$C_{16}$ esters, such as isohexyl neopentanoate;
synthetic esters, such as oils of formula $R^1COOR^2$ in which $R^1$ represents a higher fatty acid residue comprising from 6 to 29 carbon atoms and $R^2$ represents a hydrocarbon-based chain containing from 3 to 30 carbon atoms, such as purcellin oil, isopropyl myristate, 2-ethylhexyl palmitate, isostearyl neopentanoate, isopropyl myristate, isopropyl stearate, isopropyl lanolate, isotridecyl isononanoate, 2-octyldodecyl stearate, 2-octyldodecyl erucate, isostearyl isostearate, arachidyl propionate, 2-octyldodecyl benzoate;
hydroxylated esters, such as isostearyl lactate, octyl hydroxystearate, octyldodecyl hydroxystearate, diisostearyl malate, triisocetyl citrate;
polyol esters such as propylene glycol dioctanoate, neopentyl glycol diheptanoate, diethylene glycol diisononanoate and pentaerythritol esters; and/or mixtures thereof, fatty alcohols containing from 12 to 16 carbon atoms, such as octyldodecanol, 2-butyloctanol, 2-hexyldecanol, 2-undecylpentadecanol and oleyl alcohol, hydrocarbon-based plant oils, such as liquid triglycerides of fatty acids, caprylic/capric acid triglycerides, such as those sold by the company Stearineries Dubois or those sold under the names Miglyol 810, 812 and 818 by the company Dynamit Nobel, or alternatively wheat germ oil, corn oil, sunflower oil, karite oil, castor oil, sweet almond oil, macadamia oil, apricot oil, soybean oil, cotton oil, alfalfa oil, poppy oil, pumpkin oil, sesame oil, marrow oil, avocado oil, hazelnut oil, grapeseed oil, blackcurrant seed oil, evening primrose oil, millet oil, barley oil, quinoa oil, olive oil, rye oil, safflower oil, sandalwood oil, passion flower oil, musk rose oil; these plant oils have the particular feature of being liquid at a temperature of less than or equal to 25° C., oils of mineral, plant or animal origin, such as liquid petroleum jelly, soybean oil, sunflower oil, sesame oil, rapeseed oil, sweet almond oil, macadamia oil, blackcurrant seed oil, karite butter and its liquid fraction, or perhydrosqualene, hydrocarbon-based oils, such as hydrogenated isoparaffins, for instance parleam and in particular volatile $C_8$–$C_{16}$ isoparaffinic oils such as isododecane, isodecane and isohexadecane, fluoro oils, among which mention may be made of perfluoropolyethers, such as the products sold under the trade name "Fomblin" by the company Montefluos, as well as fluoro silicones, such as trifluoromethyl($C_1$–$C_4$) alkyl dimethicones, for example the product sold under the trade name "X22819" by the company Shin Etsu, and/or mixtures thereof.

The oily phase can comprise, for example, from 5 to 20% by weight, relative to the total weight of the composition, of fatty alcohols. In one embodiment of the present invention, the oily phase comprises at least one fatty ester other than isononyl isononanoate in a content which can range from 0.1 to 30%, more preferably from 5 to 20%, by weight relative to the total weight of the composition.

According to one embodiment of the invention, the oily phase consists solely of a mixture of isononyl isononanoate and at least one silicone oil. According to another embodiment of the invention, the oily phase consists solely of isononyl isononanoate, at least one fatty ester other than isononyl isononanoate and at least one silicone oil.

The isononyl isononanoate is present in a content of at least 15% by weight, preferably at least 30% by weight, relative to the total weight of the oily phase.

The compositions according to the invention also comprise a particulate phase comprising at least one pulverulent compound chosen from pigments, nacres, and fillers known to be used in cosmetic compositions. The at least one pulverulent compound is present in a content of at least 10% by weight, relative to the total weight of the composition.

The fillers which may be present in the composition in a proportion of 5–40% by weight, relative to the total weight of the composition, can be mineral or synthetic, and lamellar or non-lamellar. In one embodiment of the invention, the fillers are present in a content of from 10 to 25% by weight relative to the total weight of the composition.

As fillers, mention may be made of talc, mica, silica, kaolin, Teflon (polytetrafluoroethylene), starch, natural Mother-of-pearl, boron nitride, microspheres such as Expancel (Nobel Industrie) and microsponges such as Polytrap (Dow Corning). Spherical fillers such as polyethylene powders, Nylon powders, silicone resin microbeads (Tospearls from Toshiba) and silica microspheres can also be used.

According to one embodiment of the present invention, microspheres are used, and in particular microspheres of silica, Teflon, Nylon, talc, mica, kaolin, or mixtures thereof.

The pigments can be present in the composition in a content ranging from 0.1 to 30% by weight, relative to the total weight of the composition. They can be white or coloured, and mineral and/or organic. Among the mineral pigments which may be mentioned are titanium dioxide, zirconium dioxide and cerium dioxide, as well as zinc oxide, iron oxide, chromium oxide, ferric blue, nacres such as mica coated with titanium oxide, with iron oxide, with natural pigment or with bismuth oxychloride, as well as coloured titanium mica and/or mixtures thereof. Among the organic pigments which may be mentioned are carbon black and barium, strontium, calcium and aluminium lakes and/or mixtures thereof. The pigments can also have a hydrophobic surface or can be treated so as to make their surface hydrophobic; this treatment can be carried out according to the methods known to those skilled in the art; in particular, the pigments can be coated with silicone compounds such as polydimethylsiloxanes (PDMSs) and/or with polymers, in particular polyethylenes and/or amino acids.

Among the coated pigments which may be mentioned in particular are the pigments sold under the name "SA" by the company Miyoshi (PDMS-coated pigments).

The pigments thus coated can be incorporated into the composition according to the invention in a proportion of between 0.1 and 30% by weight relative to the total weight of the composition. In one embodiment of the invention, the pigments are present in a content of at least 2% by weight, preferably 8 to 15%, relative to the total weight of the composition.

The nacres can be present in the composition in the proportion of 0–30% by weight, preferably 10 to 20% by weight. Among the nacres which can be envisaged, mention may be made of natural Mother-of-pearl, mica coated with titanium oxide, with iron oxide, with natural pigment or with bismuth oxychloride, as well as coloured titanium mica.

The compositions according to the invention can also comprise fatty substances other than the oils mentioned above, for instance waxes or pasty fatty substances. The term "wax" means a fatty substance which is solid at room temperature.

The pasty fatty substances can be defined with the aid of at least one of the physicochemical properties below:
  a viscosity of from 0.1 to 40 Pa.s (1 to 400 poises), measured at 40° C. with a Contraves TV rotary viscometer fitted with an MS-r3 or MS-r4 rotor at a frequency of 60 Hz,
  a melting point of 25–70° C., preferably 25–55° C.

As waxes which can be used according to the invention, mention may be made of:
  waxes of animal origin, such as beeswax, spermaceti, lanolin wax and lanolin derivatives, plant waxes such as carnauba wax, candelilla wax, ouricury wax, Japan wax, cocoa butter, cork fibre waxes or sugar cane wax,
  mineral waxes, for example paraffin wax, petroleum jelly wax, lignite wax or microcrystalline waxes or ozokerites,
  synthetic waxes, including polyethylene waxes, polytetrafluoroethylene waxes and the waxes obtained by Fisher-Tropsch synthesis,
  silicone waxes, in particular substituted linear polysiloxanes; mention may be made, for example, of polyether silicone waxes, alkyl- or alkoxydimethicones containing from 16 to 45 carbon atoms, alkylmethicones such as the $C_{30}$–$C_{45}$ alkylmethicone sold under the trade name "AMS C 30" by Dow Corning,
  hydrogenated oils that are solid as 25° C., such as hydrogenated castor oil, hydrogenated jojoba oil, hydrogenated palm oil, hydrogenated tallow, hydrogenated cocoa oil and fatty esters that are solid at 25° C. such as $C_{20}$–$C_{40}$ alkyl stearate sold under the trade name "Kester Wax K82H" by the company Koster Keunen,
  and/or mixtures thereof.

In one embodiment of the present invention, polyethylene waxes, microcrystalline waxes, carnauba waxes, hydrogenated jojoba oil, candelilla waxes and/or mixtures thereof will be used. The waxes are present in a content of at least 5% by weight, preferably from 6 to 15%, relative to the total weight of the composition.

These fatty substances can be chosen in particular in a varied manner by a person skilled in the art in order to prepare a composition which has the desired properties, for example in terms of consistency or texture.

Among the other liposoluble adjuvants which can be incorporated into the composition, mention may be made of lipophilic UV screening agents, vitamins and other lipophilic cosmetic active agents, antioxidants, fragrances and ceramides.

The composition according to the invention can also comprise a cosmetically, pharmaceutically or hygienically acceptable medium. In this case, it can comprise any additive usually used in the cosmetics, pharmaceutical or hygiene field, such as antioxidants, dyes, fragrances, essential oils, preserving agents, cosmetic active agents, moisturizers, vitamins, sphingolipids, liposoluble polymers, in particular hydrocarbon-based liposoluble polymers, such as polybutene, polyalkylenes, polyacrylates and silicone polymers that are compatible with fatty substances.

These additives can be present in the composition in a proportion of 0–15% by weight. Needless to say, a person skilled in the art will take care to select this or these optional additional compound(s), and/or the amount thereof, such that the advantageous properties of the composition according to the invention are not, or are not substantially, adversely affected by the addition envisaged.

The compositions according to the invention can be in the form of a cosmetic product and in particular in the form of a care product for the body and/or the face and/or the scalp or alternatively a make-up product, in particular a foundation, a concealer, a face powder, an eyeshadow, an eyeliner, a mascara or a lipstick, or a make-up product for the body. The compositions according to the invention can be in the form of a fluid cream or a stick, or in the form of a soft paste.

The compositions according to the invention are prepared according to the conventional methods for preparing anhydrous compositions that are well known to those skilled in the art. Preferably, the compositions according to the invention are cast products manufactured by melting the waxes and then adding the other components of the composition, and finally by casting in a dish. In one embodiment of the invention, the composition according to the invention is a cast foundation.

The invention will be illustrated more clearly with the aid of the following examples, which in no way limit the present invention. In all these examples, the amounts are given as percentages by weight, relative to the total weight of the composition.

EXAMPLE 1: Comparative

The following compositions were prepared:

| | |
|---|---|
| isononyl isononanoate | x% |
| 2-ethylhexyl palmitate | qs 100% |
| isopropyl lanolate | 5% |
| waxes | 6% |
| pigments | 22% |

-continued

| | |
|---|---|
| Nylon powder | 16% |
| PTFE wax | 7% |
| silicone oil (polydimethylsiloxane) | 8% | with:

| Composition | % of isononyl isononanoate |
|---|---|
| Composition A (invention) | 10 |
| Composition B (comparative) | 5 |

The adjustment to 100% was effected by the percentage of 2-ethylhexyl palmitate.

Compositions A and B can, for example, be foundations. They were prepared according to the following procedure: the pigments were ground in the silicone. The waxes were then heated until molten. The fatty esters, the pigments ground in the silicone and then the fillers were added to the waxes, with continuous heating. Finally, the mixture was poured into a dish.

Composition A was easier to spread; it was softer and easier to make up with than composition B. In addition, its texture was finer and it was more pleasant.

EXAMPLE 2: Comparative

Compositions C, according to the invention, and D, E and F, not in accordance with the invention (identical to C but in which the isononyl isononanoate was replaced with another oily ester) were prepared as follows:

| Composition | |
|---|---|
| oily ester | 30% |
| 2-ethylhexyl palmitate | 7% |
| isopropyl lanolate | 5% |
| plant waxes | 6% |
| pigments | 22% |
| Nylon powder | 16% |
| PTFE wax | 7% |
| silicone oil (polydimethylsiloxane) | 7% | with:

| Composition | Oily ester |
|---|---|
| Composition C (invention) | Isononyl isononanoate |
| Composition D (comparative) | Isotridecyl isononanoate |
| Composition E (comparative) | 2-Ethylhexyl palmitate |
| Composition F (comparative) | Isostearyl neopentanoate |

Compositions C to F were prepared according to the same procedure as in Example 1.

Composition C was very soft. It spread particularly well. The make-up result obtained with composition C was more natural, it marked the dry zones and the pores less than the make-up result obtained with compositions D to F. Composition C was less oily and less sticky when applied than compositions D to F. The texture of composition C was finer and the product remained less at the surface than with compositions D to F.

EXAMPLE 3

Composition A of Example 1 was prepared, replacing 5% of isopropyl lanolate with 5% of silicone oil (polydimethylsiloxane). The composition obtained was soft and spread particularly well. It did not feel sticky or greasy when applied.

What is claimed is:

1. An anhydrous composition comprising
   (a) an oily phase comprising
      (i) isononyl isononanoate in a content of at least 10% by weight, relative to the total weight of the composition; and
      (ii) at least one a silicone oil present in a content of at least 5% by weight, relative to the total weight of the composition; and
   (b) a particulate phase comprising at least one pulverulent compound present in a content of at least 10% by weight, relative to the total weight of the composition.

2. A composition according to claim 1, wherein said isononyl isononanoate is present in a content of greater than 10% by weight, relative to the total weight of the composition.

3. A composition according to claim 1, wherein said isononyl isononanoate is present in a content ranging from 10 to 40% by weight, relative to the total weight of the composition.

4. A composition according to claim 1, wherein said isononyl isononanoate is present in a content ranging from 15 to 35% by weight, relative to the total weight of the composition.

5. A composition according to claim 1, wherein said isononyl isononanoate is present in a content of at least 15% by weight, relative to the total weight of the oily phase.

6. A composition according to claim 1, wherein said isononyl isononanoate is present in a content of at least 30% by weight, relative to the total weight of the oily phase.

7. A composition according to claim 1, wherein said oily phase consists of a mixture of said isononyl isononanoate and said at least one silicone oil.

8. A composition according to claim 1, wherein the oily phase further comprises at least one fatty ester other than isononyl isononanoate.

9. A composition according to claim 8, wherein said at least one fatty ester other than isononyl isononanoate is present in a content ranging from 0.1 to 30% by weight, relative to the total weight of the composition.

10. A composition according to claim 8, wherein said at least one fatty ester other than isononyl isononanoate is present in a content ranging from 5 to 20% by weight, relative to the total weight of the composition.

11. A composition according to claim 8, wherein said oily phase consists of a mixture of said isononyl isononanoate, said at least one fatty ester other than isononyl isononanoate, and said at least one silicone oil.

12. A composition according to claim 8, wherein said at least one fatty ester other than isononyl isononanoate is chosen from branched $C_8$–$C_{16}$ esters, synthetic esters, hydroxylated esters, and polyol esters.

13. A composition according to claim 12, wherein said branched $C_8$–$C_{16}$ esters is isohexyl neopentanoate.

14. A composition according to claim 12, wherein said synthetic esters are chosen from esters of the formula $R^1COOR^2$, wherein $R^1$ represents a higher fatty acid residue comprising from 6 to 29 carbon atoms and $R^2$ represents a hydrocarbon-based chain containing from 3 to 30 carbon atoms.

15. A composition according to claim 14, wherein said synthetic esters of the formula $R^1COOR^2$ are chosen from purcellin oil, isopropyl myristate, 2-ethylhexyl palmitate, isostearyl neopentanoate, isopropyl myristate, isopropyl stearate, isopropyl lanolate, isotridecyl isononanoate, 2-octyidodecyl stearate, 2-octyldodecyl erucate, isostearyl isostearate, arachidyl propionate and 2-octyidodecyl benzoate.

16. A composition according to claim 12, wherein said hydroxylated esters are chosen from isostearyl lactate, octyl hydroxystearate, octyldodecyl hydroxystearate, diisostearyl malate, and triisocetyl citrate.

17. A composition according to claim 12, wherein said polyol esters are chosen from propylene glycol dioctanoate, neopentyl glycol diheptanoate, diethylene glycol diisononanoate and pentaerythritol esters.

18. A composition according to claim 1, wherein said at least one silicone oil is present in a content ranging from 5 to 55% by weight, relative to the total weight of the composition.

19. A composition according to claim 1, wherein said at least one silicone oil is present in a content ranging from 5 to 25% by weight, relative to the total weight of the composition.

20. A composition according to claim 1, wherein said at least one silicone oil is present in a content ranging from 10 to 25% by weight, relative to the total weight of the composition.

21. A composition according to claim 1, wherein said at least one silicone oil is chosen from:

a) cyclic volatile silicones containing from 3 to 8 silicon atoms;

b) linear volatile silicones containing from 2 to 9 silicon atoms;

c) polydimethylsiloxanes of the general formula below:

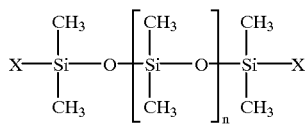

in which:

X is —CH$_3$ or OH, and n is an integer ranging from 0 to 2000;

d) alkylmethylpolysiloxanes;

e) cyclocopolymers of the dimethylsiloxane/methylalkylsiloxane type;

f) silicone gums which are optionally phenylated or hydroxylated polysiloxanes, with a high molecular mass of about 200,000 to 1,000,000 and with a viscosity of greater than 500,000 mPa.s, when they are dissolved in a solvent; and g) silicone resins comprising a combination of units $R_3SiO_{1/2}$, $R_2SiO_{2/2}$, $RSiO_{3/2}$ and $SiO_{4/2}$, in which R is hydrogen, a $C_1$–$C_6$ alkyl radical or a phenyl radical, when they are dissolved in a solvent.

22. A composition according to claim 21, wherein said at least one silicone oil is chosen from cyclic volatile silicones containing from 4 to 6 silicon atoms.

23. A composition according to claim 21, wherein said cyclic volatile silicones are chosen from cyclotetradimethylsiloxane, cyclopentadimethylsiloxane and cyclohexadimethylsiloxane.

24. A composition according to claim 21, wherein the viscosity of said polydimethylsiloxanes at 25° C. is less than or equal to 0.06 m$^2$/s.

25. A composition according to claim 21, wherein said alkylmethylpolysiloxanes are chosen from poly($C_1$–$C_{20}$) alkylsiloxanes.

26. A composition according to claim 25, wherein said poly($C_1$–$C_{20}$)alkylsiloxanes are chosen from phenylsilicone oils and cetyldimethicone.

27. A composition according to claim 1, wherein said composition does not contain phenyltrimethicone.

28. A composition according to claim 1, wherein said at least one pulverulent compound is chosen from fillers, pigments, and nacres.

29. A composition according to claim 28, wherein said fillers are chosen from microspheres.

30. A composition according to claim 29, wherein said microspheres are chosen from silica, teflon, nylon, talc, mica and kaolin.

31. A composition according to claim 28, wherein said fillers are present in a content ranging from 5 to 40% by weight relative to the total weight of the composition.

32. A composition according to claim 28, wherein said fillers are present in a content ranging from 10 to 25% by weight relative to the total weight of the composition.

33. A composition according to claim 28, wherein said pigments are chosen from titanium dioxide, zirconium dioxide and cerium dioxide, zinc oxide, iron oxide and chromium oxide, ferric blue, carbon black, barium, strontium, calcium and aluminium lakes, pigments coated with silicone compounds and pigments coated with polymers.

34. A composition according to claim 33, wherein said polymers coating said pigments are chosen from polyethylenes, amino acids, and mixtures thereof.

35. A composition according to claim 28, wherein said pigments are present in a content of at least 2% by weight, relative to the total weight of the composition.

36. A composition according to claim 28, wherein said pigments are present in a content of between about 8 to 15% by weight, relative to the total weight of the composition.

37. A composition according to claim 1, wherein said composition further comprises at least one wax.

38. A composition according to claim 37, wherein said at least one wax is chosen from a) waxes of animal origin;

b) plant waxes;

c) mineral waxes;

d) synthetic waxes;

e) silicone waxes; and f) hydrogenated oils that are solid at 25° C.

39. A composition according to claim 38, wherein said waxes of animal origin are chosen from beeswax, spermaceti, lanolin wax and lanolin derivatives.

40. A composition according to claim 38, wherein said plant waxes are chosen from carnauba wax, candelilla wax, ouricury wax, Japan wax, cocoa butter, cork fibre wax and sugar cane wax.

41. A composition according to claim 38, wherein said mineral waxes are chosen from paraffin wax, petroleum jelly wax, lignite wax, microcrystalline waxes and ozokerites.

42. A composition according to claim 38, wherein said synthetic waxes are chosen from polyethylene waxes, polytetrafluoroethylene waxes and the waxes obtained by Fisher-Tropsch synthesis.

43. A composition according to claim 38, wherein said silicone waxes are chosen from substituted linear polysiloxanes; polyether silicone waxes, alkyl- or alkoxydimethicones containing from 16 to 45 carbon atoms, and alkyl methicones.

44. A composition according to claim 38, wherein said hydrogenated oils are chosen from hydrogenated castor oil, hydrogenated jojoba oil, hydrogenated palm oil, hydrogenated tallow, hydrogenated cocoa oil and fatty esters that are solid at 25° C.

45. A composition according to claim 44, wherein said fatty esters that are solid at 25° C. are chosen from $C_{20}$–$C_{40}$ alkyl stearates.

46. A composition according to claim 37, wherein said at least one wax is present in a content of at least 5% by weight, relative to the total weight of the composition.

47. A composition according to claim 37, wherein said at least one wax is present in a content of between about 6 to 15%, relative to the total weight of the composition.

48. A composition according to claim 1, wherein said composition is a cosmetic, dermatological, hygiene or pharmaceutical composition.

49. A composition according to claim 1, wherein said composition is in the form of a make-up product.

50. A composition according to claim 49, wherein said make-up product is a foundation, a concealer, a face powder, an eyeshadow, an eyeliner, a mascara, a lipstick, or a make-up product for the body.

51. A non-therapeutic treatment process for the skin, mucous membrane, scalp, or mixtures thereof comprising applying an anhydrous composition to said skin, mucous membrane, scalp, or mixtures thereof, said anhydrous composition comprising (a) an oily phase comprising
   (i) isononyl isononanoate in a content of at least 10% by weight, relative to the total weight of the composition; and
   (ii) at least one a silicone oil present in a content of at least 5% by weight, relative to the total weight of the composition; and (b) a particulate phase comprising at least one pulverulent compound present in a content of at least 10% by weight, relative to the total weight of the composition.

* * * * *

UNITED STATES PATENT AND TRADEMARK OFFICE
CERTIFICATE OF CORRECTION

PATENT NO.   : 6,344,205 B1
DATED        : February 5, 2002
INVENTOR(S)  : Sabine Grimm et al.

It is certified that error appears in the above-identified patent and that said Letters Patent is hereby corrected as shown below:

<u>Column 8</u>,
Line 65, "2-octyidodecyl stearate" should read -- 2-octyldodecyl stearate --.
Line 66, "and 2-octyidodecyl" should read -- and 2-octyldodecyl --.

Signed and Sealed this

Thirtieth Day of April, 2002

Attest:

*Attesting Officer*

JAMES E. ROGAN
*Director of the United States Patent and Trademark Office*